United States Patent
Nimura et al.

(10) Patent No.: US 11,964,083 B2
(45) Date of Patent: Apr. 23, 2024

(54) EXTRACORPOREAL CIRCULATION CASSETTE

(71) Applicant: NIKKISO CO., LTD., Tokyo (JP)

(72) Inventors: Hiroshi Nimura, Makinohara (JP); Yoshimichi Masuda, Makinohara (JP); Masato Fujiwara, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 1011 days.

(21) Appl. No.: 16/077,532

(22) PCT Filed: Feb. 6, 2017

(86) PCT No.: PCT/JP2017/004170
§ 371 (c)(1),
(2) Date: Aug. 13, 2018

(87) PCT Pub. No.: WO2017/141747
PCT Pub. Date: Aug. 24, 2017

(65) Prior Publication Data
US 2019/0054225 A1  Feb. 21, 2019

(30) Foreign Application Priority Data
Feb. 18, 2016 (JP) ................ 2016-028737

(51) Int. Cl.
*A61M 1/16* (2006.01)
*A61M 1/14* (2006.01)
(Continued)

(52) U.S. Cl.
CPC ...... *A61M 1/1621* (2014.02); *A61M 1/15632* (2022.05); *A61M 1/16* (2013.01);
(Continued)

(58) Field of Classification Search
CPC .. A61M 1/1621; A61M 1/1668; A61M 1/267; A61M 1/3626; A61M 1/3639; A61M 1/3663; A61M 2205/12
See application file for complete search history.

(56) References Cited

U.S. PATENT DOCUMENTS

| 4,436,620 A | 3/1984 | Bellotti et al. |
| 5,441,636 A | 8/1995 | Chevallet et al. |

(Continued)

FOREIGN PATENT DOCUMENTS

| GB | 2110564 A | 6/1983 |
| JP | H06292722 A | 10/1994 |

(Continued)

OTHER PUBLICATIONS

Definition of slot, www.merriam-webster.com/dictionary/slot.*
(Continued)

*Primary Examiner* — Jessica Arble
(74) *Attorney, Agent, or Firm* — Chiesa Shahinian & Giantomasi PC

(57) ABSTRACT

This extracorporeal circulation cassette is provided with: a blood circuit (10) comprising a flexible tube and having a blood tube access portion set in a predetermined position in a device; a dialysate circuit (12) comprising a flexible tube and having a dialysate tube access portion set in a predetermined position in the device; a first panel (4) and a second panel (6) that are rigid and that integrate the blood circuit (10) and the dialysate circuit (12) while sandwiching the blood circuit (10) and the dialysate circuit (12) from both sides; and a window portion formed in a part of at least one of the first panel (4) and the second panel (6), disposed in a predetermined position in the device. The blood tube access portion and the dialysate tube access portion are positioned in the window portion.

19 Claims, 13 Drawing Sheets

(51) Int. Cl.
*A61M 1/26* (2006.01)
*A61M 1/36* (2006.01)

(52) U.S. Cl.
CPC ........ *A61M 1/1652* (2014.02); *A61M 1/1668* (2014.02); *A61M 1/267* (2014.02); *A61M 1/36226* (2022.05); *A61M 1/362264* (2022.05); *A61M 1/3626* (2013.01); *A61M 1/3639* (2013.01); *A61M 1/3663* (2013.01); *A61M 1/36222* (2022.05); *A61M 2205/12* (2013.01); *A61M 2205/14* (2013.01); *A61M 2205/6018* (2013.01)

(56) References Cited

U.S. PATENT DOCUMENTS

| 6,554,789 | B1 | 4/2003 | Brugger et al. | |
|---|---|---|---|---|
| 6,743,201 | B1 | 6/2004 | Doenig et al. | |
| 7,686,779 | B1* | 3/2010 | Gibbs | A61M 1/30 604/6.01 |
| 2002/0147423 | A1 | 10/2002 | Burbank et al. | |
| 2005/0209563 | A1* | 9/2005 | Hopping | A61M 1/281 604/151 |
| 2005/0230292 | A1* | 10/2005 | Beden | A61M 1/15632 210/321.71 |
| 2007/0078370 | A1* | 4/2007 | Shener | A61M 3/022 604/8 |
| 2007/0278155 | A1* | 12/2007 | Lo | A61M 1/166 210/646 |
| 2009/0101566 | A1* | 4/2009 | Crnkovich | A61M 1/3641 210/249 |
| 2009/0124963 | A1* | 5/2009 | Hogard | A61M 1/1613 604/30 |
| 2009/0230043 | A1 | 9/2009 | Heyes et al. | |
| 2010/0292628 | A1* | 11/2010 | Powers | A61M 1/3639 73/756 |
| 2011/0009797 | A1 | 1/2011 | Kelly et al. | |
| 2011/0315611 | A1 | 12/2011 | Fulkerson et al. | |
| 2017/0021077 | A1* | 1/2017 | Yamazaki | B29C 49/02 |

FOREIGN PATENT DOCUMENTS

| JP | 2008539849 A | 11/2008 |
|---|---|---|
| JP | 4197795 B2 | 12/2008 |
| JP | 2014516255 A | 7/2014 |
| JP | 2016-022226 A | 2/2016 |

OTHER PUBLICATIONS

Notice of Reasons for Refusal dated Aug. 17, 2021, in connection with Japanese Patent Application No. 2018-500045, 8 pgs (including translation).

Communication pursuant to Article 94(3) EPC dated Dec. 1, 2020, in connection with European Patent Application No. 17753007.8, filed Feb. 6, 2017, 6 pgs.

Extended Search Report dated Sep. 6, 2019, in connection with European Patent Application No. 17753007.8, 7 pgs.

International Search Report and Written Opinion dated Mar. 7, 2017, in connection with International Patent Application No. PCT/JP2017/004170, 8 pgs. English translation of Written Opinion is currently unavailable.

* cited by examiner

EXTRACORPOREAL CIRCULATION CASSETTE

CROSS-REFERENCE TO RELATED APPLICATIONS

This application is a U.S. national phase filing under 35 U.S.C. § 371 of International Application No. PCT/JP2017/004170 filed Feb. 6, 2017, which claims priority to Japanese Patent Application No. 2016-028737, filed Feb. 18, 2016, the disclosures of which are incorporated herein by reference in their entirety.

TECHNICAL FIELD

The present invention relates to extracorporeal circulation cassettes used in blood purification therapy.

BACKGROUND ART

Blood purification apparatuses such as hemodialyzers and hemofiltration apparatuses have been used for carrying out extracorporeal circulation and purification therapy of blood of patients. In these blood purification apparatuses, a blood circuit, a dialysate circuit, a blood purification unit, and the like have to be replaced and re-installed every time the patient receives treatment, thus making the installation procedures of such circuits and units be cumbersome. To increase the operation efficiency, therefore, the blood circuit, the dialysate circuit, and the like are unified and installed as a unit on the blood purification apparatus.

In one example, the blood circuit, the dialysate circuit, and the like are unified by adhering a tube forming the blood circuit to a panel, and installing the panel with the tube to a housing of the blood purification apparatus. Alternatively, a method of integrally forming a fluid path and the like forming the blood circuit in a cassette is also known (see Patent Literature 1).

CITATION LIST

Patent Literature

Patent Literature 1: JP 4197795 B2

SUMMARY OF INVENTION

Technical Problem

When using the method of bonding the tube or the like forming the blood circuit to the panel, the position of the tube can be determined by bonding the tube to the panel. However, the tube is exposed on the periphery of the panel and would interrupt installation on the blood purification apparatus. This decreases operability. Meanwhile, when using the method of integrally forming the fluid path and the like, which form the blood circuit, in a cassette, the structure of the cassette would be complicated and the extracorporeal circulation cassette itself becomes costly.

It is an object of the present invention to provide an extracorporeal circulation cassette having an excellent installation and removing operability at low cost.

Solution to Problem (1) An extracorporeal circulation cassette including a blood circuit formed of a flexible tube and including a blood tube access portion which is set at a predetermined position of an apparatus, first and second panels unified with each other by sandwiching the blood circuit from both sides and having rigidity, and a window formed at a portion disposed at the predetermined position of at least one of the first and second panels of the apparatus, in which the blood tube access portion of the blood circuit stored in a space formed by the first and second panels is disposed at the window.

(2) The extracorporeal circulation cassette according to (1), in which the portion disposed at the predetermined position of the apparatus is inserted into the apparatus.

(3) The extracorporeal circulation cassette according to (1) or (2), in which at least part of the portion other than the blood tube access portion of the blood circuit is disposed in the space formed by the first and second panels.

(4) The extracorporeal circulation cassette according to any one of (1) to (3), further including a dialysate circuit formed of a flexible tube and including a dialysate tube access portion which is set at the predetermined position of the apparatus, in which the dialysate circuit is stored in the space formed by the first and second panels, and the dialysate tube access portion of the dialysate circuit is disposed at the window.

(5) The extracorporeal circulation cassette according to (4), in which at least part of the portion other than the dialysate tube access portion of the dialysate circuit is disposed in the space formed by the first and second panels.

(6) The extracorporeal circulation cassette according to (4) or (5), in which the window has an opening, and the blood tube access portion of the blood circuit and the dialysate tube access portion of the dialysate circuit are exposed at the opening.

(7) The extracorporeal circulation cassette according to any one of (1) to (6), in which the blood tube access portion is set at a prescribed position of, a blood flow rate controller that controls a flow rate of blood, a bubble detector that detects bubbles, a pressure detector that detects pressure, a blood detector that detects blood, a clamp unit that closes the blood tube access portion, or a flow rate detector that detects a flow rate of blood.

(8) The extracorporeal circulation cassette according to any one of (4) to (6), in which the dialysate tube access portion is set at a prescribed position of a dialysate flow rate controller that controls a flow rate of dialysate, a blood detector that detects blood, a pressure detector that detects pressure, a clamp unit that closes the dialysate tube access portion, or a flow rate detector that detects a flow rate of dialysate.

(9) The extracorporeal circulation cassette according to any one of (1) to (8), in which one side shape of the first and second panels unified each other is asymmetric to the other side shape thereof.

(10) The extracorporeal circulation cassette according to any one of (1) to (8), in which one side of the first and second panels unified with each other has different thicknesses from the other side thereof.

(11) The extracorporeal circulation cassette according to any one of (1) to (8), in which the first and second panels unified with each other include a guide to be fitted into a rail formed in a cassette slot of the apparatus at one side and the other side.

(12) The extracorporeal circulation cassette according to any one of (1) to (8), in which the portion of at least one of the first and second panels to be inserted into the apparatus includes a cassette-side fitting portion fitted to a cassette-slot-side fitting portion formed in a cassette slot of the apparatus.

(13) The extracorporeal circulation cassette according to any one of (1) to (12), in which the first and second panels are formed by bending a single panel.

(14) The extracorporeal circulation cassette according to any one of (1) to (13), further including a blood purification unit.

(15) The extracorporeal circulation cassette according to (14), in which a space is formed between the blood purification unit and the first and second panels.

(16) The extracorporeal circulation cassette according to any one of (1) to (15), further including narrow portions provided on at least one of the first and second panels and fitted to connectors connected on both ends of the blood tube access portion and both ends of the dialysate tube access portion.

Advantageous Effects of Invention

With the extracorporeal circulation cassette according to (1), the blood circuit formed of the flexible tube is stored in the space formed by the first and second panels having rigidity, and the blood tube access portion of the blood circuit is disposed at the window of the first and second panels. Thus, positioning at the predetermined position of the apparatus can be facilitated, and the blood tube access portion can be positioned accurately. In addition, the blood circuit is stored in the space formed by the first and second panels. This structure enables manufacturing of the extracorporeal circulation cassette at low cost.

With the extracorporeal circulation cassette according to (2), the blood circuit formed of the flexible tube is stored in the space formed by the first and second panels having rigidity, and the blood tube access portion of the blood circuit is disposed at the window of the first and second panels. Thus, insertion into the apparatus is facilitated and the positioning of the blood tube access portion can be carried out accurately.

With the extracorporeal circulation cassette according to (3), at least part of the portion of the blood circuit other than the blood tube access portion is disposed in the space formed by the first and second panels. This facilitates insertion without being interrupted by the tube during arrangement at the predetermined position of the apparatus.

With the extracorporeal circulation cassette according to (4), the dialysate circuit made of the flexible tube is stored in the space formed by the first and second panels, and the dialysate tube access portion of the dialysate circuit is located at the window of the first and second panels. This facilitates insertion without being interrupted by the tube during arrangement at the predetermined position of the apparatus.

With the extracorporeal circulation cassette according to (5), at least part of the portion of the dialysate circuit other than the dialysate tube access portion is located in the space formed by the first and second panels. This facilitates insertion without being interrupted by the tube during the arrangement at the predetermined position of the apparatus, and achieves accurate positioning of the dialysate tube access portion.

With the extracorporeal circulation cassette according to (6), the blood tube access portion of the blood circuit and the dialysate tube access portion of the dialysate circuit are exposed at the opening, so that the blood tube access portion and the dialysate tube access portion can be set at the predetermined positions.

With the extracorporeal circulation cassette according to (7), the blood tube access portion can be set accurately at the prescribed position of the blood flow rate controller that controls a flow rate of the blood, the bubble detector that detects bubbles, the pressure detector that detects pressure, the blood detector that detects blood, the clamp unit that closes the dialysate tube access portion, or the flow rate detector that detects a flow rate of the blood.

With the extracorporeal circulation cassette according to (8), the dialysate tube access portion can be set accurately at the prescribed position of the dialysate flow rate controller that controls a flow rate of the dialysate, the blood detector that detects blood, the pressure detector that detects pressure, the clamp unit that closes the dialysate tube access portion, or the flow rate detector that detects a flow rate of the dialysate.

With the extracorporeal circulation cassette according to (9), one side shape of the first and second panels unified each other is asymmetric to the other side shape thereof. Thus, insertion of the extracorporeal circulation cassette in a wrong direction can be prevented when the extracorporeal circulation cassette is loaded into the cassette slot of the apparatus.

With the extracorporeal circulation cassette according to (10), one side of the first and second panels unified with each other has different thicknesses from the other side thereof. Thus, insertion of the extracorporeal circulation cassette in a wrong direction can be prevented when the extracorporeal circulation cassette is loaded into the cassette slot of the apparatus.

With the extracorporeal circulation cassette according to (11), the operability can improve in inserting the extracorporeal circulation cassette into the cassette slot.

With the extracorporeal circulation cassette according to (12), the completion of insertion of the extracorporeal circulation cassette into the cassette slot can be sensed. This improves operability.

With the extracorporeal circulation cassette according to (13), the first and second panels are formed by bending a single panel. This reduces manufacturing costs.

With the extracorporeal circulation cassette according to (14), the blood purification unit, as well as the blood circuit and the dialysate circuit, can be installed on and removed from the apparatus. This further improves the operability in installation/removal.

With the extracorporeal circulation cassette according to (15), the space is formed between the blood purification unit and the first and second panels, so that the extracorporeal circulation cassette can be installed on and removed from the apparatus, with the blood purification unit being held by hand.

With the extracorporeal circulation cassette according to (16), connectors coupled to both ends of the blood tube access portion and the dialysate tube access portion can be fixed to the narrow portions. This improves assembling efficiency of the extracorporeal circulation cassette.

DESCRIPTION OF EMBODIMENTS

Figure 1:
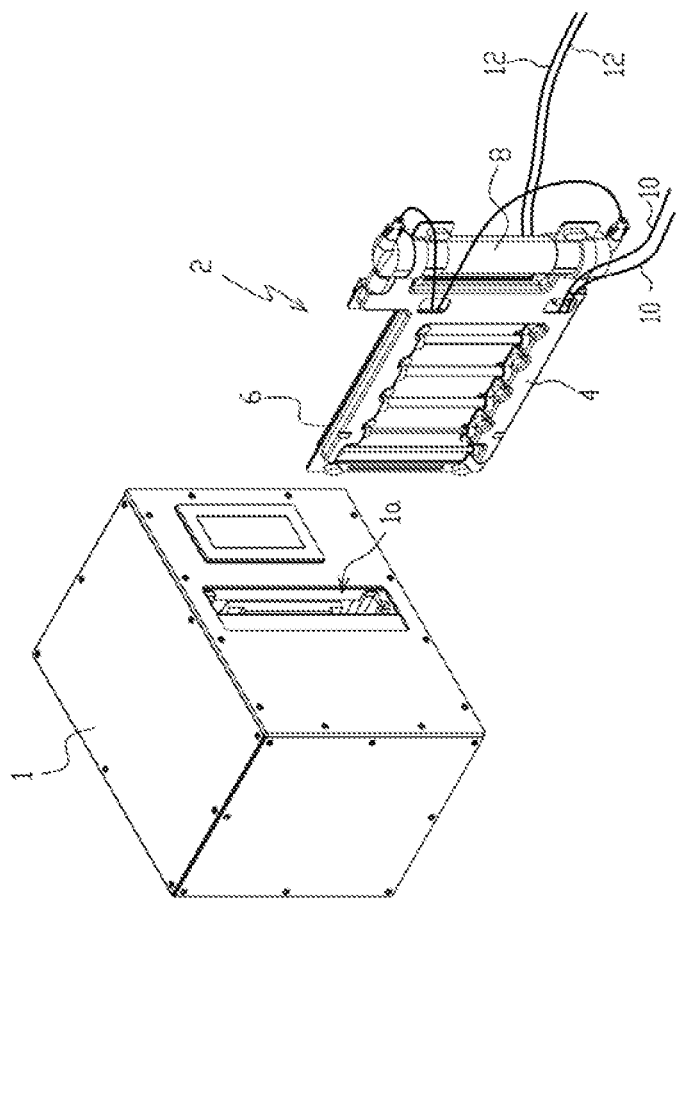
FIG. 1 is a perspective view of a blood purification apparatus and an extracorporeal circulation cassette according to an embodiment.

In the following, an extracorporeal circulation cassette that can be detachably installed on a blood purification apparatus according to an embodiment will be described by referring to the accompanying drawings. FIG. 1 is a perspective view of a blood purification apparatus and an extracorporeal circulation cassette. As illustrated in FIG. 1, a blood purification apparatus 1 has a cassette slot 1a on its front face, into which an extracorporeal circulation cassette 2 is inserted and mounted.

Figure 2:
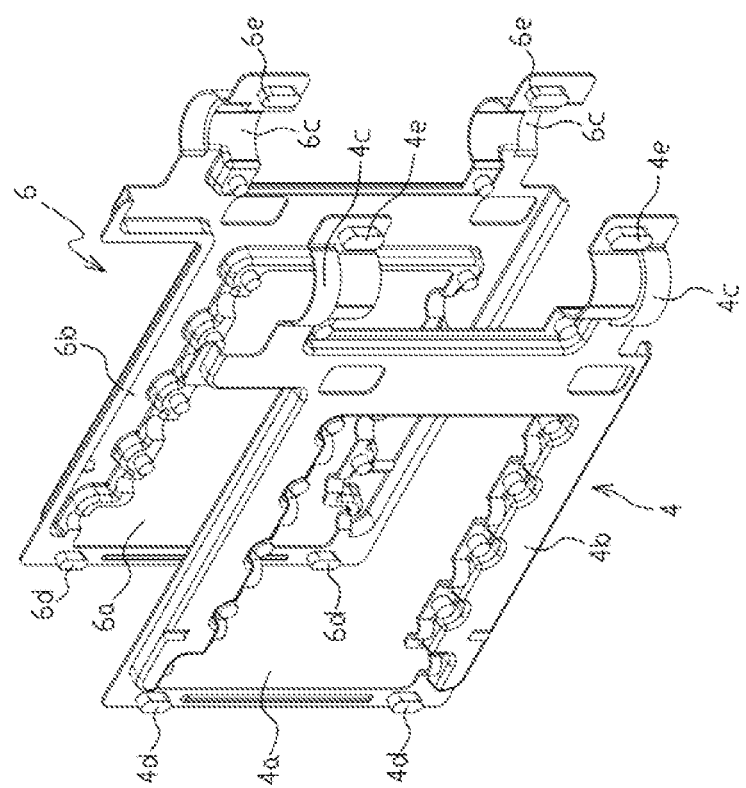
FIG. 2 is a perspective view of panels (before unification) forming the extracorporeal circulation cassette according to the embodiment.

The extracorporeal circulation cassette 2 includes a first panel 4 and a second panel 6, both having rigidity. As illustrated in FIG. 2, the first panel 4 includes a tube storage portion 4b having a rectangular shape in a planar view. The tube storage portion 4b has an opening 4a used as a window in which blood tube access portions 10a, 10b, and 10c and dialysate tube access portions 12a and 12b, which are described later, are set at predetermined positions, when the blood purification apparatus 1 carries out internal sensing or controls a flow rate of the liquid in the tubes from outside of the blood tube access portions 10a, 10b, and 10c or the dialysate tube access portions 12a and 12b. The opening 4a is formed in approximately the center of the tube storage portion 4b and inserted into the cassette slot 1a when the extracorporeal circulation cassette 2 is loaded into the cassette slot 1a of the blood purification apparatus 1.

The tube storage portion 4b has two holding portions 4c that extend to one side (upper portion of FIG. 2) and the other side (lower portion of FIG. 2) of one end portion (right end portion of FIG. 2) and that hold a dialyzer (blood purification unit) 8. In contrast, the tube storage portion 4b has fitting recesses 4d used for unification with the second panel 6 on one side and the other side of the other end portion (left end portion of FIG. 2), and the tube storage portion 4b has fitting recesses 4e used for unification with the second panel 6 at each end of the two holding portions 4c.

The second panel 6 has a shape corresponding to the first panel 4, as illustrated in FIG. 2. Specifically, the second panel 6 includes a tube storage portion 6b having a rectangular shape in a planar view. The tube storage portion 6b has an opening 6a used as a window in which blood tube access portions 10a, 10b, and 10c and dialysate tube access portions 12a and 12b are set at predetermined positions, when the blood purification apparatus 1 carries out internal sensing or controls a flow rate of the liquid in the tubes from outside of the blood tube access portions 10a, 10b, and 10c or the dialysate tube access portions 12a and 12b. The opening 6a is formed in approximately the center of the tube storage portion 6b corresponding to the opening 4a and inserted into the cassette slot 1a when the extracorporeal circulation cassette 2 is loaded into the cassette slot 1a of the blood purification apparatus 1.

The tube storage portion 6b has two holding portions 6c that extend to one side (upper portion of FIG. 2) and the other side (lower portion of FIG. 2) of one end (right end portion of FIG. 2) and that hold the dialyzer 8. In contrast, the tube storage portion 6b has fitting projections 6d used for unification with the first panel 4 on one side and the other side of the other end portion (left end portion of FIG. 2), and the tube storage portion 6b has fitting projections 6e used for unification with the first panel 4 at each end of the two holding portions 6c.

Figure 3:
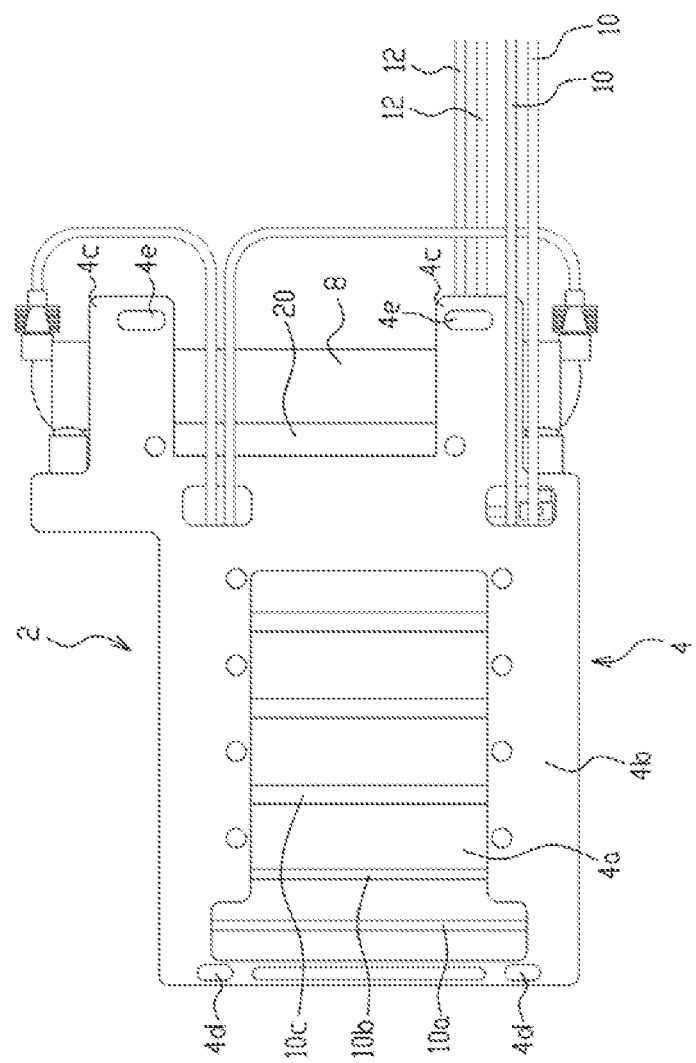
FIG. 3 is a front view of the extracorporeal circulation cassette according to the embodiment.

As illustrated in FIG. 3, the first and second panels 4 and 6 sandwich a blood circuit 10 formed of a flexible tube and a dialysate circuit 12 formed of a flexible tube with the tube storage portion 4b of the first panel 4 and the tube storage portion 6b of the second panel 6, thus storing the blood circuit 10 and the dialysate circuit 12 in a space formed between the tube storage portion 4b and the tube storage portion 6b. A dialyzer 8 is held by holding portions 4c and 6c. The first and second panels 4 and 6 are unified by fitting the fitting recesses 4d formed in the tube storage portion 4b and the fitting recesses 4e formed in the holding portions 4c of the first panel 4 to the fitting projections 6d formed in the tube storage portion 6b and the fitting projections 6e formed in the holding portions 6c of the second panel 6.

The holding portions 4c and 6c each extend from one ends of the tube storage portions 4b and 6b. By unifying the first and second panels 4 and 6 and holding the dialyzer 8 in the holding portions 4c and 6c, a predetermined space 20 is generated between the dialyzer 8 and one ends of the tube storage portions 4b and 6b.

The holding portions 4c extending at the one side of the tube storage portion 4b of the first panel 4 and the holding portions 6c extending at the one side of the tube storage portion 6b of the second panel 6 are disposed outside the one sides of the tube storage portions 4b and 6b. Therefore, the unified first and second panels 4 and 6 is shaped asymmetrically, that is, the shape of the one side of each panel (the shape of the unified first and second panels 4 and 6 in the upper portion of FIG. 2) is asymmetric to the shape of the other side of each panel (the shape of the unified first and second panels 4 and 6 in the lower portion of FIG. 2).

Figure 4:
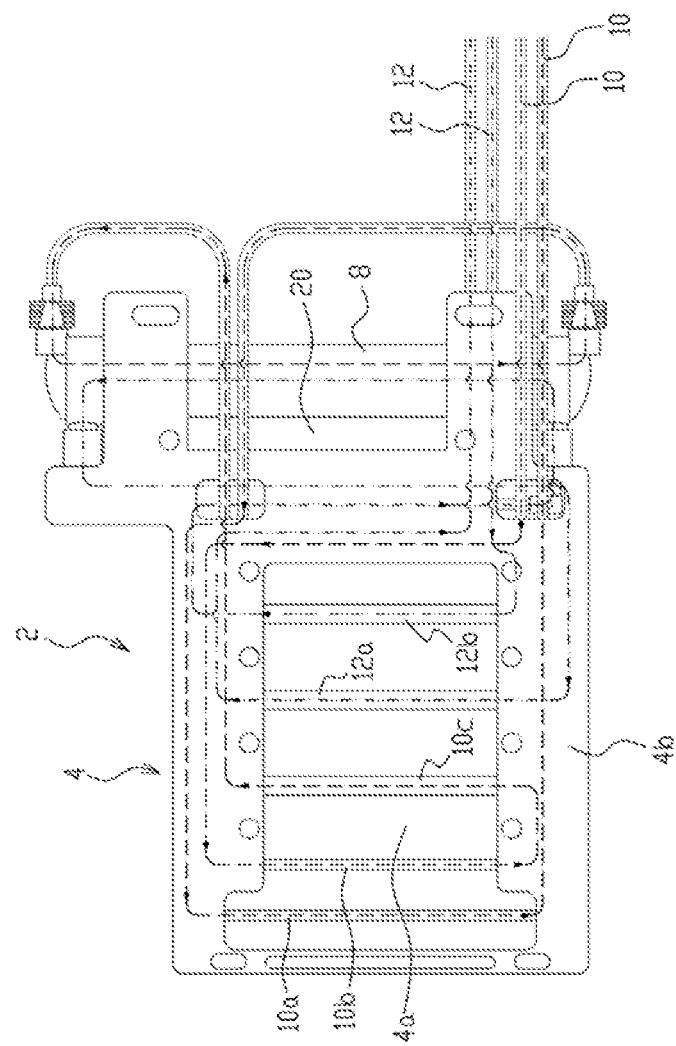
FIG. 4 illustrates a blood circuit and a dialysate circuit which are stored in the extracorporeal circulation cassette according to the embodiment.

As illustrated in FIG. 4, the blood circuit 10 is connected to the dialyzer 8 on the way, and including the blood tube access portions 10a, 10b, and 10c that are set at prescribed positions of, for example, an air bubble detector (not illustrated) that detects air bubbles or a pressure detector (not illustrated) that detects a pressure by the blood purification apparatus 1. The blood circuit 10 is stored in the space formed by the tube storage portions 4b and 6b, with the blood tube access portions 10a, 10b, and 10c being located and exposed at the window formed by the openings 4a and 6a.

The blood tube access portions 10a and 10b are set at prescribed positions at which the detection of air bubbles and pressure can be directly carried out by the air bubble detector detecting air bubbles and the pressure detector detecting pressure. The blood tube access portion 10c is set at a prescribed position at which the flow rate of the blood can be directly controlled by a blood pump (not illustrated) that serves as a flow rate controller controlling the flow rate of blood in the blood circuit 10.

The portion of the blood circuit 10 other than the blood tube access portions 10a, 10b, and 10c is stored in the portion other than the openings 4a and 6a of the tube storage portions 4b and 6b, respectively, that is, in the space formed by the tube storage portions 4b and 6b around the openings 4a and 6a.

When the extracorporeal circulation cassette 2 is loaded into the cassette slot 1a of the blood purification apparatus 1, the portion of the extracorporeal circulation cassette 2 that is not inserted into the cassette slot 1a reveals a part of the blood circuit 10 other than the blood tube access portions 10a, 10b, and 10c. Alternatively, the part of the blood circuit 10 other than the blood tube access portions 10a, 10b, and 10c may be exposed at the space formed by the openings 4a and 6a.

Meanwhile, the dialysate circuit 12 has dialysate tube access portions 12a and 12b on the way that are set at predetermined positions of, for example, a dialysate pump (not illustrated) by the blood purification apparatus 1. The dialysate circuit 12 is stored in the space formed by the tube storage portions 4b and 6b with the dialysate tube access portions 12a and 12b being located and exposed at the window formed by the openings 4a and 6a.

The dialysate tube access portions 12a and 12b are respectively set at predetermined positions such that a dialysate pump, which serves as a flow rate controller that controls the flow rate of the dialysate, can directly control the flow rate of the dialysate in the dialysate circuit 12. The portion of the dialysate circuit 12 other than the dialysate tube access portions 12a and 12b is stored in the portion other than the openings 4a and 6a of the tube storage portions 4b and 6b, respectively, that is, in the space formed by the tube storage portions 4b and 6b around the openings 4a and 6a.

When the extracorporeal circulation cassette 2 is loaded into the cassette slot 1a of the blood purification apparatus 1, the portion of the extracorporeal circulation cassette 2 that is not inserted into the cassette slot 1a reveals a part of the dialysate circuit 12 other than the dialysate tube access portions 12a and 12b. Alternatively, the portion of the dialysate circuit 12 other than the dialysate tube access portions 12a and 12b may be exposed to the space formed by the openings 4a and 6a.

The blood pump to be used may be implemented by a finger pump that strokes the blood tube access portion 10c with fingers. The dialysate pump to be used may be implemented by a finger pump that strokes the dialysate tube access portions 12a and 12b with fingers.

Figure 5:
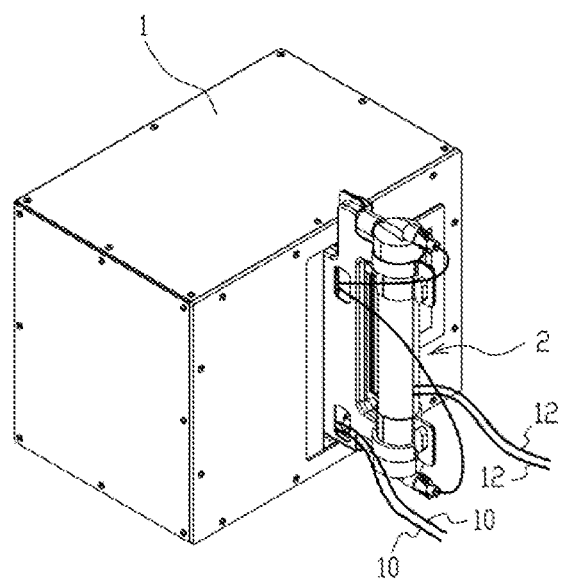
FIG. 5 is a perspective view of the blood purification apparatus with the extracorporeal circulation cassette being set therein according to the embodiment.

FIG. 5 is a perspective view of the blood purification apparatus with the extracorporeal circulation cassette being set therein. When the extracorporeal circulation cassette 2 is inserted and loaded into the cassette slot 1a of the blood purification apparatus 1, the blood tube access portions 10a, 10b, and 10c and the dialysate tube access portions 12a and 12b are set at the predetermined positions in the blood purification apparatus 1. Specifically, the blood tube access portions 10a and 10b are set at the positions capable of being detected by the air bubble detector and the pressure detector, respectively, and the blood tube access portion 10c is set at the position at which the blood pump can control the blood flow rate. The dialysate tube access portions 12a and 12b are set at the positions at which the dialysate pump can control the flow rate of the dialysate.

With the extracorporeal circulation cassette 2 of the present embodiment, the blood circuit 10 and the dialysate circuit 12 formed of flexible tubes are stored in the space formed by the first and second panels 4 and 6 having rigidity. At least part of the blood circuit 10 and at least part of the dialysate circuit 12 other than the blood tube access portions and the dialysate tube access portions, respectively, are disposed at the positions other than the windows. Thus, the extracorporeal circulation cassette 2 can be inserted into the cassette slot 1a of the blood purification apparatus 1 easily without being interrupted by the tubes.

In addition, the blood tube access portions 10a, 10b, and 10c of the blood circuit 10 and the dialysate tube access portions 12a and 12b of the dialysate circuit 12 are disposed at the windows of the first and second panels 4 and 6, so that the blood tube access portions 10a, 10b, and 10c and the dialysate tube access portions 12a and 12b can be set accurately at the predetermined positions. Further, the blood circuit 10 and the dialysate circuit 12 are stored in the space generated by unifying the first and second panels 4 and 6. This structure enables manufacturing of the extracorporeal circulation cassette 2 at low cost.

Meanwhile, with the extracorporeal circulation cassette 2 of the present embodiment, one side shape of the first and second panels 4 and 6 unified each other is asymmetric to the other side shape thereof. This prevents insertion of the extracorporeal circulation cassette 2 in a wrong direction when the extracorporeal circulation cassette 2 is loaded into the cassette slot 1a of the blood purification apparatus 1.

Meanwhile, with the extracorporeal circulation cassette of the present embodiment, the space 20 is formed between the dialyzer 8 and the first and second panels 4 and 6, so that the extracorporeal circulation cassette 2 can be installed on and removed from the blood purification apparatus 1 with the dialyzer 8 being held by hand.

In the present embodiment, the blood circuit 10 and the dialysate circuit 12 are stored in the space formed by unifying the two panels, i.e., the first and second panels 4 and 6. Alternatively, a single panel may be bent to form the first and second panels for storing the blood circuit 10 and the dialysate circuit 12 therein. This structure can further reduce the manufacturing cost.

Although the blood circuit 10 and the dialysate circuit 12 are stored in the space formed by the first and second panels 4 and 6 in the above-described embodiment, only the blood circuit 10 may be stored in the space.

In addition, the openings are provided as windows in the first and second panels 4 and 6 in the above-described embodiment. Alternatively, entirety of the windows may be covered by thin sheet-like members made of the same material as and formed integrally with the first and second panels 4 and 6. In other words, the blood tube access portions 10a, 10b, and 10c and the dialysate tube access portions 12a and 12b may be connected with each other with sheet-like members made of the same material as the material of the first and second panels 4 and 6. In this case, the blood tube access portions 10a, 10b, and 10c and the dialysate tube access portions 12a and 12b may be formed integrally with the sheet-like members covering the windows.

Further, the extracorporeal circulation cassette 2 including the dialyzer (blood purification unit) 8 for hemodialysis has been described in the embodiment described above. Alternatively, the extracorporeal circulation cassette may not include the dialyzer 8. Alternatively, another blood purification unit may be provided instead of the dialyzer 8.

In the extracorporeal circulation cassette 2 of the embodiment described above, the thickness of the one side and the thickness of the other side of the unified part of the first and second panels 4 and 6 may be different. That is, the thickness of the one end portion of the extracorporeal circulation cassette 2 illustrated in the upper portion of FIG. 2 (the thickness between outer walls of the first and second panels 4 an 6 in the upper portion of FIG. 2) may be different from the thickness of the other end portion illustrated in the lower portion (the thickness between outer walls of the first and second panels 4 and 6 in the lower portion of FIG. 2). Such a structure can prevent insertion of the extracorporeal circulation cassette 2 in the wrong direction when the extracorporeal circulation cassette 2 is loaded into the cassette slot 1a of the blood purification apparatus 1.

Further, in the above-described embodiment, the windows are formed by the openings 4a and 6a at the corresponding part of the first and second panels 4 and 6, respectively, of the extracorporeal circulation cassette 2. Alternatively, the window may be formed by the opening either at the first panel 4 or second panel 6 of the extracorporeal circulation cassette 2.

Further, in the above-described embodiment, the first and second panels 4 and 6 each include the windows in approximately the center of the tube storage portions 4b and 6b, respectively. Alternatively, the windows may be provided on the periphery of the first and second panels 4 and 6, instead of in the center of the tube storage portions 4b and 6b.

Further, in the above-described embodiment, the blood tube access portions 10a and 10b are set at the prescribed positions of the air bubble detector and the pressure detector, respectively. Alternatively, the blood tube access portions 10a and 10b may be set at prescribed positions of, for example, the blood flow rate controller (blood pump) that controls the flow rate of the blood, the blood detector that detects blood, the clamp unit that closes the blood tube access portions, and the flow rate detector that detects the flow rate of the blood. In other words, the blood tube access portions 10a and 10b may be set at the prescribed positions, such as the position at which the blood flow rate controller (blood pump) can control the flow rate of the blood, the position at which the clamp unit can clamp, or the position that the blood detector or the flow rate detector can sense.

Further, the blood tube access portion 10c is set at the prescribed position of the blood flow rate controller (blood pump). Alternatively, the blood tube access portion 10c may be set at the prescribed positions of, for example, the blood detector that detects the blood, the clamp unit that closes the blood tube access portions, the flow rate detector that detects the flow rate of the blood, the air bubble detector, or the pressure detector. In other words, the blood tube access portion 10c can be set at the prescribed position, such as the position that can be sensed by the blood detector, the flow rate detector, the air bubble detector, or the pressure detector, or the position that can be clamped by the clamp unit.

Further, the dialysate tube access portions 12a and 12b are set at prescribed positions of the dialysate flow rate controller (dialysate pump). Alternatively, the dialysate tube access portions 12a and 12b may be set at the prescribed positions of, for example, the blood detector that detects the blood, the pressure detector that detects the pressure, the clamp unit that closes the dialysate tube access portions, or the flow rate detector that detects the flow rate of the dialysate. In other words, the dialysate tube access portions 12a and 12b may be set at the prescribed positions, such as the positions that can be sensed by the blood detector, the pressure detector, or the flow rate detector, or the position that can be clamped by the clamp unit.

Further, in the above-described embodiment, the first and second panels 4 and 6 are unified by fitting the fitting recesses 4d formed in the tube storage portion 4b and the fitting recesses 4e formed in the holding portions 4c of the first panel 4 to the fitting projections 6d formed in the tube storage portion 6b and the fitting projections 6e formed in the holding portions 6c of the second panel 6. Alternatively, the first and second panels 4 and 6 may be unified by bonding with an adhesive or the like.

Further, in the above-described embodiment, the extracorporeal circulation cassette 2 is formed of the first and second panels 4 and 6 both having rigidity. Alternatively, the first and second panels 4 and 6 having rigidity may be made of resins, and any material having rigidity can be used.

Further, in the above-described embodiment, the blood tube access portions 10a, 10b, and 10c and the dialysate tube access portions 12a and 12b are arranged in the window of the first panel 4 or second panel 6 of the extracorporeal circulation cassette 2 in this order from the other end portion side of the extracorporeal circulation cassette 2. Alternatively, the blood tube access portion 10a, 10b, and 10c and the dialysate tube access portions 12a and 12b may be arranged in a different order.

Further, in the above-described embodiment, the cassette slot 1a having a vertically-extending opening is provided in the front surface of the blood purification apparatus 1. Alternatively, the cassette slot may have a horizontally-extending opening so that the extracorporeal circulation cassette 2 can be inserted horizontally into the cassette slot.

Figure 6:
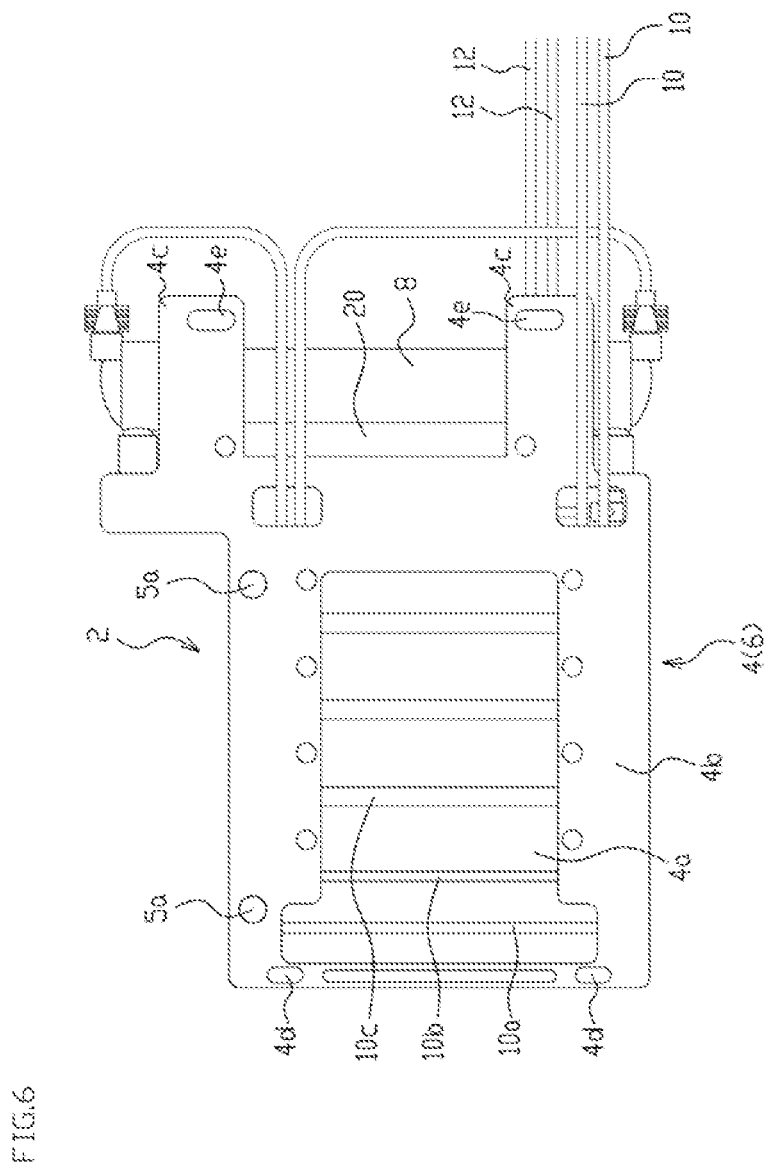
FIG. 6 is a front view of the extracorporeal circulation cassette according to the embodiment.
Figure 7:
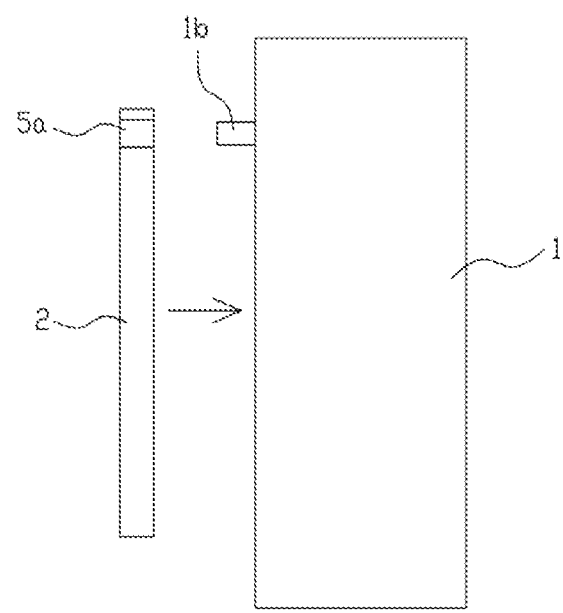
FIG. 7 illustrates how the extracorporeal circulation cassette according to the embodiment is disposed at a predetermined position of the blood purification apparatus.

Further, the extracorporeal circulation cassette 2 of the above-described embodiment is inserted into the cassette slot 1a of the blood purification apparatus 1. Alternatively, the extracorporeal circulation cassette 2 may also be disposed at a predetermined position of the blood purification apparatus 1 by hanging the extracorporeal circulation cassette 2 on the wall surface of the blood purification apparatus 1. Specifically, as illustrated in FIG. 6, two through holes 5a may be formed in the extracorporeal circulation cassette 2, and two bosses 1b may be formed on the side wall or the like of the blood purification apparatus 1. The two bosses 1b are made to penetrate through the two through holes 5a, as illustrated in FIG. 7, so that the extracorporeal circulation cassette 2 can hang on the bosses 1b of the blood purification apparatus 1 and can be disposed at the predetermined position of the blood purification apparatus 1. In this structure, the blood tube access portions 10a, 10b, and 10c and the dialysate tube access portions 12a and 12b are set at the predetermined positions of the blood purification apparatus 1 by hanging the extracorporeal circulation cassette 2 on the bosses 1b of the blood purification apparatus 1. Further, this structure can decrease the size of the blood purification apparatus 1 in the width direction (left-to-right direction in FIG. 7). Further, the method of hanging the extracorporeal circulation cassette 2 on the blood purification apparatus 1 facilitates cleaning and maintenance.

The number of the through holes 5a and the positions at which the through holes 5a are provided can be selected as needed such that the blood tube access portion 10a, 10b, and 10c and the dialysate tube access portions 12a and 12b can be set at the predetermined positions of the blood purification apparatus 1. Further, the number of the bosses 1b to be formed in the blood purification apparatus 1 is determined on the basis of the number of the through holes 5a, and the bosses 1b are formed at such positions that the blood tube access portions 10a, 10b, and 10c and the dialysate tube access portions 12a and 12b can be set at the predetermined positions in the blood purification apparatus 1.

Figure 8:
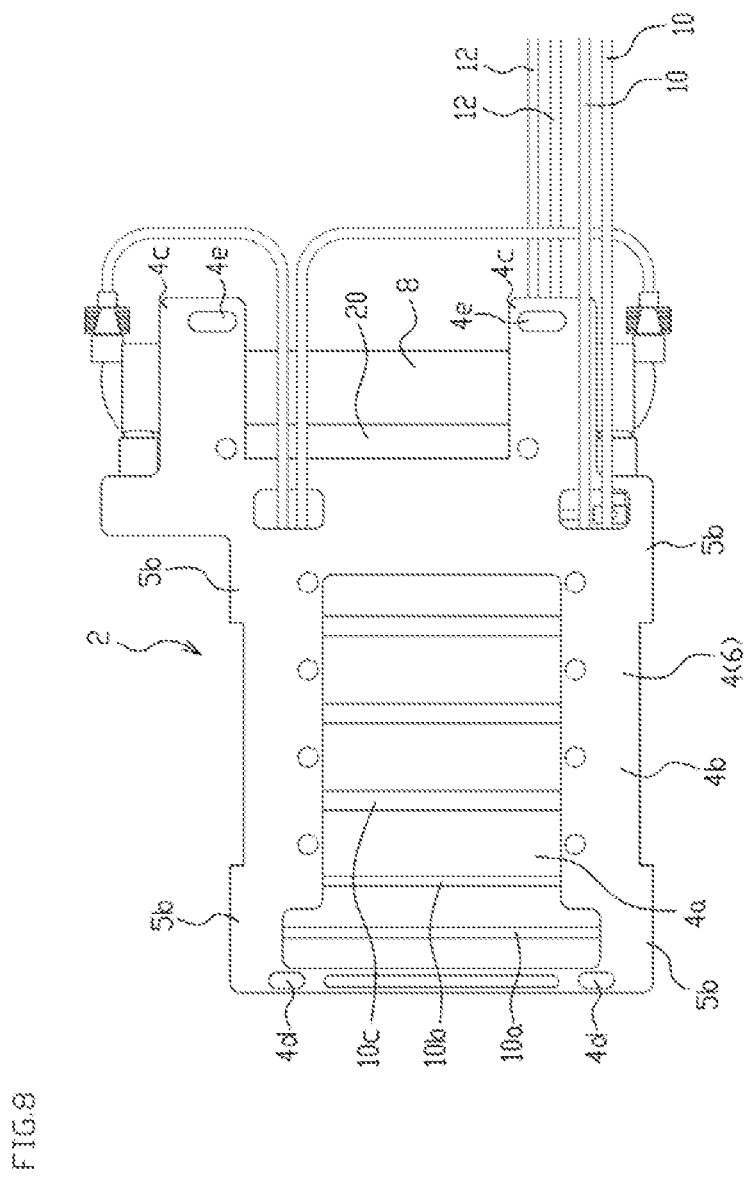
FIG. 8 is a front view of the extracorporeal circulation cassette according to the embodiment.
Figure 9:
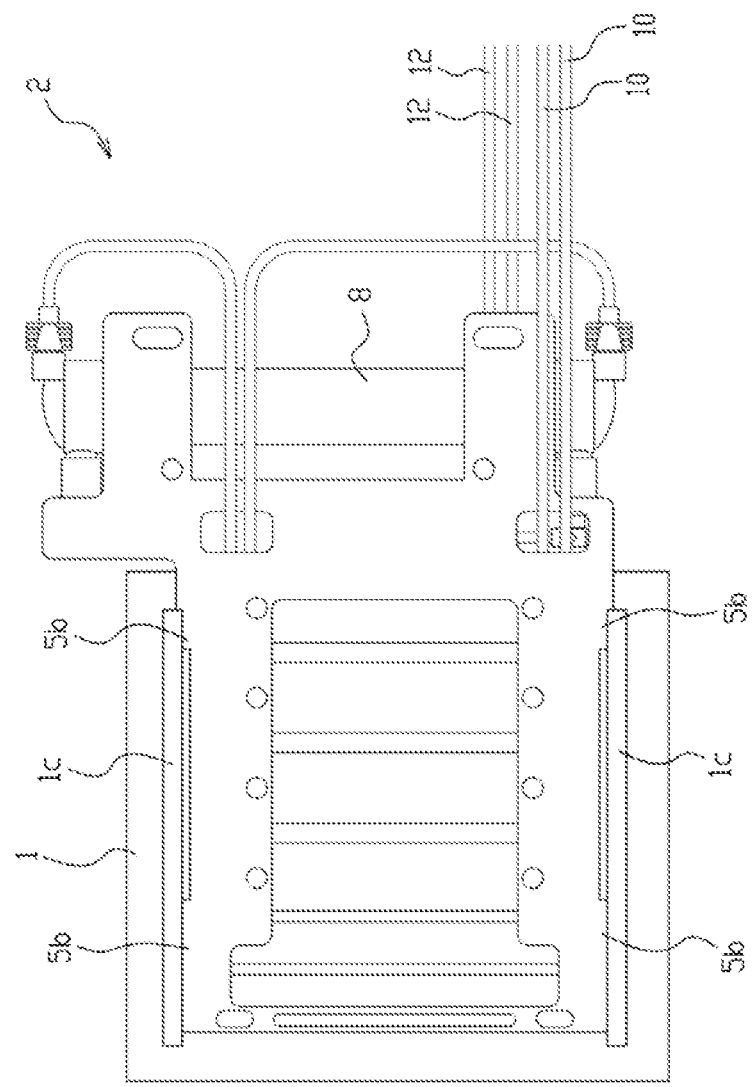
FIG. 9 illustrates the extracorporeal circulation cassette when inserted into a cassette slot.

Further, in the above-described embodiment, the unified part of the first and second panels forming the extracorporeal circulation cassette 2 may include a guide that can be fitted into a rail provided in the cassette slot 1a of the blood purification apparatus 1. Specifically, as illustrated in FIG. 8, a guide 5b is formed on both one and the other sides of the unified part of the first and second panels 4 and 6. Then, as illustrated in FIG. 9, when the extracorporeal circulation cassette 2 is inserted into the cassette slot 1a formed in the blood purification apparatus 1, the guides 5b formed on the one and the other sides of the unified part of the first and second panels 4 and 6 can be fitted into rails 1c provided inside the cassette slot 1a. FIG. 9 is the interior view of the cassette slot 1a illustrating the guides 5b being fitted into the rails 1c provided in the cassette slot 1a. The guides 5b are formed at an arbitrary position on one side and an arbitrary position on the one side of the first and second panels that are inserted into the cassette slot 1a of the extracorporeal circulation cassette 2.

By providing the guides, which are to be fitted into the rails formed in the cassette slot 1a of the blood purification apparatus 1, in the first and second panels that constitute the extracorporeal circulation cassette 2, the operability of inserting the extracorporeal circulation cassette 2 into the cassette slot 1a of the blood purification apparatus 1 can be improved.

Figure 10:
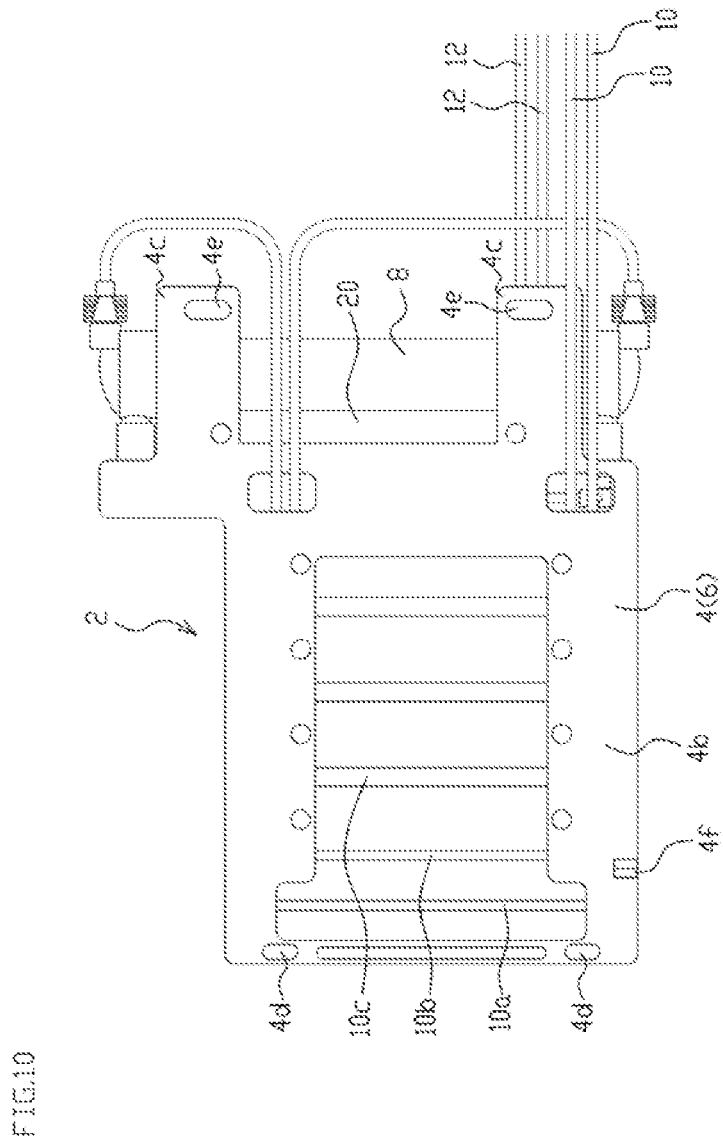
FIG. 10 is a front view of the extracorporeal circulation cassette according to the embodiment.
Figure 11:
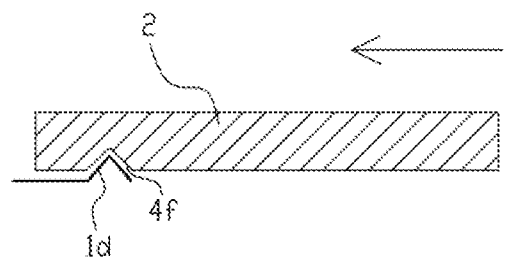
FIG. 11 illustrates how a recess in the extracorporeal circulation cassette according to the embodiment is fitted to a projection formed in the cassette slot.

Further, in the above-described embodiment, a recess serving as a cassette-side fitting portion may be formed at a portion to be inserted into the cassette slot 1a of the blood purification apparatus 1 of at least one of the first and second panels 4 and 6 forming the extracorporeal circulation cassette 2. Then, the recess can be fitted to a projection serving as a cassette-slot-side fitting portion formed in the cassette slot 1a. Specifically, as illustrated in FIG. 10, a recess 4f is provided at the portion to be inserted into the cassette slot 1a of the first panel 4. When the extracorporeal circulation cassette 2 is inserted into the cassette slot 1a of the blood purification apparatus 1 (inserted in an arrow direction in FIG. 11), the recess 4f is made to be fitted to a projection 1d such as a leaf spring provided in the cassette slot 1a. Thus, the completion of insertion of the extracorporeal circulation cassette 2 into the cassette slot 1a can be sensed. This improves operability. The recess 4f can be formed at any position inserted into the cassette slot 1a of the blood purification apparatus 1. The projection 1d provided in the cassette slot 1a is provided at a position corresponding to the recess 4f. The cassette-side fitting portion may not be provided as the recess 4f, and the cassette-slot-side fitting portion may not be provided as the projection 1d. The cassette-side fitting portion and the cassette-slot-side fitting portion need to sense the completion of insertion of the extracorporeal circulation cassette 2 into the cassette slot 1a.

Figure 12:
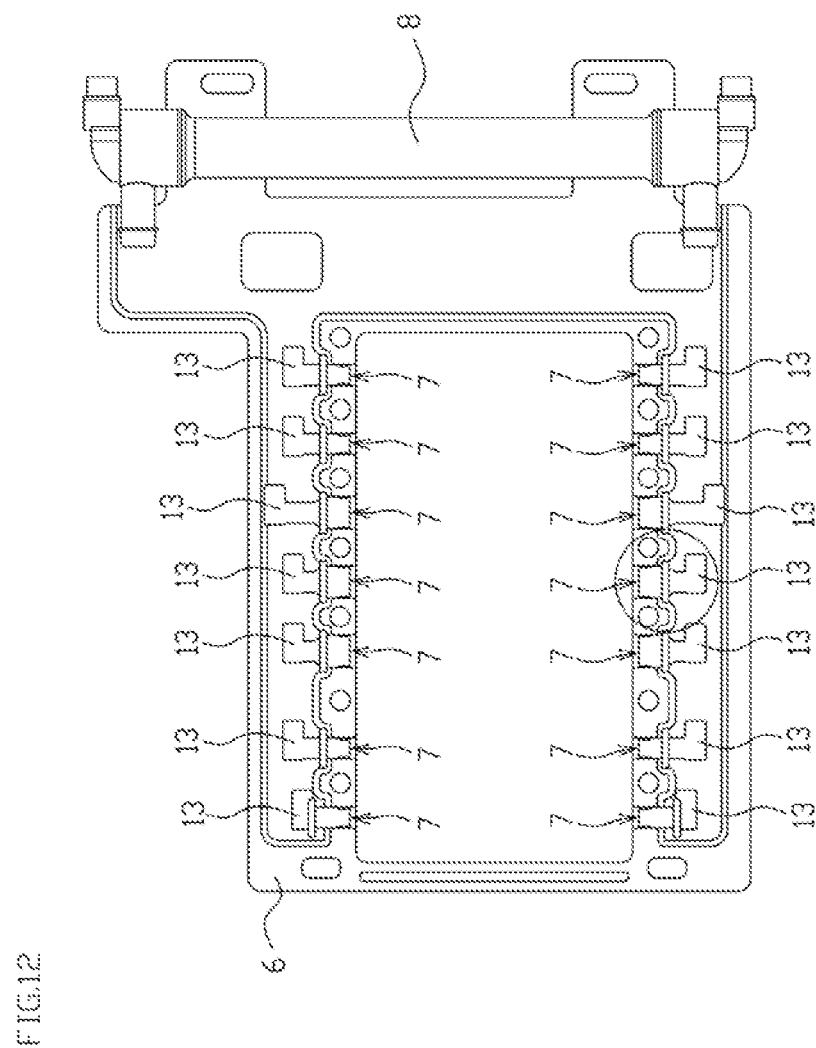
FIG. 12 illustrates fitting portions and connectors formed in the extracorporeal circulation cassette according to the embodiment.
Figure 13:
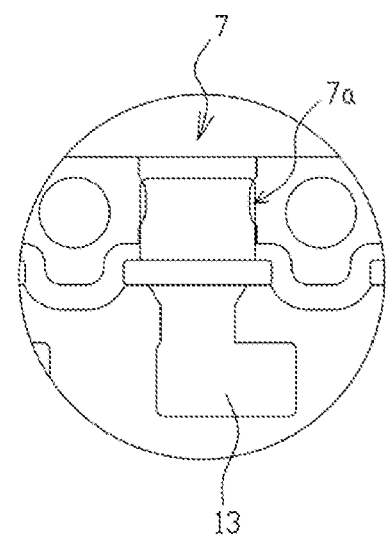
FIG. 13 illustrates a narrow portion formed in the fitting portion of the extracorporeal circulation cassette according to the embodiment.

Further, the above-described embodiment may include connectors each connected on both ends of individual blood tube access portions 10a, 10b, and 10c and both ends of individual dialysate tube access portions 12a and 12b of the extracorporeal circulation cassette 2. The embodiment may also include narrow portions for being fitted to the connectors. FIG. 12 illustrates the extracorporeal circulation cassette 2 with the first panel 4 being removed therefrom. As illustrated in this drawing, the extracorporeal circulation cassette 2 includes a plurality of fitting portions 7 for receiving connectors 13 each connected to both ends of the blood tube access portions 10a, 10b, and 10c and both ends of the dialysate tube access portions 12a and 12b. FIG. 13 is an enlarged view of an encircled portion of FIG. 12. In the fitting portion 7, a narrow portion 7a having an inner diameter smaller than an outer diameter of the connector 13 is formed. By forming such a narrow portion 7a in the fitting portion 7, the connector 13 connected to both ends of individual blood tube access portions 10a, 10b, and 10c and both ends of the dialysate tube access portions 12a and 12b can be fixed in the second panel 6. This improves assembling efficiency of the extracorporeal circulation cassette 2. The narrow portion 7a may be formed in the first panel 4, and may also be formed in both first and second panels 4 and 6.

REFERENCE SIGNS LIST

1 Blood purification apparatus
1a Cassette slot
2 Extracorporeal circulation cassette
4 First panel
4a Opening
4b Tube storage portion
4c Holding portion
4d, 4e Fitting recess
6 Second panel
6a Opening
6b Tube storage portion
6c Holding portion
6d, 6e Fitting projection
8 Dialyzer
10 Blood circuit
10a, 10b, 10c Blood tube access portion
12 Dialysate circuit
12a, 12b Dialysate tube access portion

The invention claimed is:
1. An extracorporeal circulation cassette, comprising:
a blood circuit formed of a flexible tube and including a blood tube access portion which is configured to be slidably inserted into a cassette slot of an apparatus;
first and second panels configured to contact each other in a unified configuration by sandwiching the blood circuit from both sides and having rigidity, wherein the first panel comprises a recess, the second panel comprises a projection, wherein in the unified configuration, the projection extends into at least a portion of the recess; and
a window formed at a part slidably inserted into the cassette slot of at least one of the first and second panels, wherein
the blood tube access portion of the blood circuit stored in a space formed by the first and second panels is disposed at the window, and
a part of the blood circuit other than the blood tube access portion is exposed from the cassette slot when the extracorporeal circulation cassette is in an inserted configuration in the cassette slot,
wherein the window has an opening in at least one of the first panel and the second panel, wherein the flexible tube extends through a tube opening of at least one of the first panel and the second panel between the first panel and the second panel, in the unified configuration, and wherein the tube opening is between the opening and a proximal edge of at least one of the first panel and the second panel.

2. The extracorporeal circulation cassette according to claim 1, wherein at least part of the portion other than the blood tube access portion of the blood circuit is disposed in the space formed by the first panel and the second panel, between the first panel and the second panel in the unified configuration.

3. The extracorporeal circulation cassette according to claim 1, further comprising:

a dialysate circuit formed of a flexible tube and including a dialysate tube access portion which is configured to be inserted into the cassette slot of the apparatus, wherein the dialysate circuit is stored in the space formed by the first and second panels, and the dialysate tube access portion of the dialysate circuit is disposed at the window.

4. The extracorporeal circulation cassette according to claim 3, wherein at least part of the portion other than the dialysate tube access portion of the dialysate circuit is disposed in the space formed by the first and second panels.

5. The extracorporeal circulation cassette according to claim 4, wherein the blood tube access portion of the blood circuit and the dialysate tube access portion of the dialysate circuit are exposed at the opening.

6. The extracorporeal circulation cassette according to claim 1, wherein the blood tube access portion is set at a prescribed position of a blood flow rate controller that controls a flow rate of blood, a bubble detector that detects bubbles, a pressure detector that detects pressure, a blood detector that detects blood, a clamp unit that closes the blood tube access portion, or a flow rate detector that detects a flow rate of blood.

7. The extracorporeal circulation cassette according to claim 3, wherein the dialysate tube access portion is set at a prescribed position of a dialysate flow rate controller that controls a flow rate of dialysate, a blood detector that detects blood, a pressure detector that detects pressure, a clamp unit that closes the dialysate tube access portion, or a flow rate detector that detects a flow rate of dialysate.

8. The extracorporeal circulation cassette according to claim 1, wherein one side shape of the first and second panels, in the unified configuration, is asymmetric to the other side shape thereof.

9. The extracorporeal circulation cassette according to claim 1, wherein one side of the first and second panels, in the unified configuration, has different thicknesses from the other side thereof.

10. The extracorporeal circulation cassette according to claim 1, wherein the first and second panels, in the unified configuration, include a guide, the guide configured to fit into a rail formed in the cassette slot at one side and the other side.

11. The extracorporeal circulation cassette according to claim 1, wherein the portion of at least one of the first and second panels, which is configured to be inserted into the cassette slot, includes a cassette-side fitting portion fitted to a cassette-slot-side fitting portion formed in the cassette slot.

12. The extracorporeal circulation cassette according to claim 1, wherein the first and second panels are formed by bending a single panel.

13. The extracorporeal circulation cassette according to claim 1, further comprising:

a blood purification unit.

14. The extracorporeal circulation cassette according to claim 13, wherein a space is formed between the blood purification unit and the first and second panels.

15. The extracorporeal circulation cassette according to claim 3, further comprising:

narrow portions provided on at least one of the first and second panels and fitted to connectors connected on both ends of the blood tube access portion and both ends of the dialysate tube access portion.

16. The extracorporeal circulation cassette according to claim 1, wherein the blood circuit only protrudes from one edge of the extracorporeal circulation cassette.

17. The extracorporeal circulation cassette according to claim 1, wherein the flexible tube of the blood circuit comprises an inlet tube and an outlet tube, wherein the inlet tube is configured to connect to an inlet of a blood purification unit and the outlet tube is configured to connect to an outlet of the blood purification unit.

18. The extracorporeal circulation cassette according to claim 1, wherein the first panel comprises an edge recess, and the apparatus comprises a projection, wherein, in the inserted configuration, the projection of the apparatus extends at least partially into the edge recess.

19. The extracorporeal circulation cassette according to claim 1, wherein the window has an opening in both the first panel and the second panel, wherein the recess is between the opening of the first panel and a distal edge of the first panel, and the projection is between the opening of the second panel and a distal edge of the second panel.

* * * * *